United States Patent
Okuma

(10) Patent No.: US 8,986,364 B2
(45) Date of Patent: Mar. 24, 2015

(54) STENT DELIVERY SYSTEM

(75) Inventor: Nobuaki Okuma, Tokyo (JP)

(73) Assignee: Gadelius Medical K.K., Tokyo (JP)

( * ) Notice: Subject to any disclaimer, the term of this patent is extended or adjusted under 35 U.S.C. 154(b) by 135 days.

(21) Appl. No.: 13/466,271

(22) Filed: May 8, 2012

(65) Prior Publication Data

US 2012/0303109 A1   Nov. 29, 2012

(30) Foreign Application Priority Data

May 24, 2011   (JP) ................. 2011-115752

(51) Int. Cl.
*A61F 2/06*   (2013.01)
*A61F 2/95*   (2013.01)
*A61F 2/04*   (2013.01)

(52) U.S. Cl.
CPC ............ *A61F 2/95* (2013.01); *A61F 2002/041* (2013.01); *A61F 2002/9511* (2013.01)
USPC ...................................... 623/1.11

(58) Field of Classification Search
CPC .......... A61F 2/95; A61F 2/962; A61F 2/966; A61F 2002/9511; A61F 2002/9665; A61F 2002/011
USPC ........ 623/1.11, 1.12, 1.23; 606/108, 194, 200
See application file for complete search history.

(56) References Cited

U.S. PATENT DOCUMENTS

| | | | |
|---|---|---|---|
| 5,242,452 A * | 9/1993 | Inoue ......................... 606/108 |
| 5,334,185 A | 8/1994 | Giesy et al. | |
| 6,264,624 B1 | 7/2001 | Desmond, III et al. | |
| 7,998,189 B2 * | 8/2011 | Kolbel et al. ............... 623/1.13 |
| 8,034,094 B2 * | 10/2011 | Aoba et al. .................. 623/1.11 |
| 8,298,276 B2 * | 10/2012 | Ozawa et al. ............... 623/1.11 |
| 8,506,616 B2 * | 8/2013 | Hartley et al. .............. 623/1.13 |
| 2003/0233140 A1 * | 12/2003 | Hartley et al. .............. 623/1.11 |
| 2005/0085891 A1 * | 4/2005 | Goto et al. .................. 623/1.11 |
| 2007/0293929 A1 * | 12/2007 | Aoba et al. .................. 623/1.11 |
| 2009/0143849 A1 * | 6/2009 | Ozawa et al. ............... 623/1.11 |

FOREIGN PATENT DOCUMENTS

JP   2009-297502   12/2009
WO   03-092782    4/2003

* cited by examiner

*Primary Examiner* — Kathleen Holwerda
*Assistant Examiner* — Sarah W Aleman
(74) *Attorney, Agent, or Firm* — Rankin, Hill & Clark LLP

(57) ABSTRACT

A stent delivery system has a pusher catheter having an opening to which a filament is tied to the distal end thereof, and a stent having a catching hole. Because a knot is loosely fit in the catching hole from inside, with an inner catheter supporting the loose-fitting, inadvertent uncoupling of the stent and the pusher catheter can be prevented until the inner catheter is pulled out, and the two can be easily uncoupled by pulling out the inner catheter.

10 Claims, 4 Drawing Sheets

STENT DELIVERY SYSTEM

FIELD OF THE INVENTION

This invention relates to a catheter-based stent delivery system, and specifically to a system using a tube stent (hereinafter in some cases simply referred to as a "stent") made from polyethylene, plastic, and others.

BACKGROUND

Stents used for stent placement are classified roughly into two groups: tube stents made from polyethylene, plastic, and others, and metallic stents made from metals. There are variety of tube stents, such as those with or without a side hole and a flap, straight, curved, pig-tailed tube stents.

A tube stent is pushed forward by a pusher catheter inside a human body along a guide wire or inner catheter inserted into the human body. Because a conventional tube stent is designed to be simply pushed by a pusher catheter and cannot be pulled back, a stent must be removed when the stent could not be accurately placed where it should be. This problem has led to development of delivery systems which is capable of pulling back a stent, examples of which includes inventions as shown below.

PATENT DOCUMENTS

[PATENT DOCUMENT 1] U.S. Pat. No. 5,334,185
[PATENT DOCUMENT 2] U.S. Pat. No. 6,264,624
[PATENT DOCUMENT 3] Unexamined Japanese Patent Publication No. 297502/2009

Patent document 1 discloses a delivery system in which a filament loop attached to a pusher catheter is positioned within a slot on a stent, through which an inner catheter is slid so as to secure coupling of the stent and the pusher catheter, and in which the two are uncoupled when the inner catheter is retracted and the loop is pulled out of the slot. Further, it also discloses a system in which a stent carries a tail which is captured by the loop attached to the pusher catheter to secure coupling of the two.

Patent document 2 discloses a delivery system in which the distal end of a filament loop attached to a pusher catheter is positioned within a passage of a stent, through which an inner catheter is inserted so that the stent and the pusher catheter are joined with each other.

Patent document 3 discloses a delivery system in which a filament loop attached to a pusher catheter is pierced through a hole on a stent, inserted into the inside of the pusher catheter, and locked by a locking member which is formed separately from the inner catheter so as to secure coupling of a stent and a pusher catheter, and in which the filament are pulled out with the locking member or a separate lead-in member after the inner catheter is pulled out to uncouple the stent and the pusher catheter.

The system wherein the filament loop is positioned within the slot from outside of the stent as shown in Patent Document 1 has a risk that the stent and the pusher catheter may not be uncoupled completely because the loop may not move out of the slot smoothly. The system as shown in Patent Document 3 wherein the filament loop is positioned within the passage from outside of the stent may have the same problem as stated above, because the loop may be hooked by a flap.

Further, the system as shown in Patent Document 1 in which the tail is captured by the loop has a risk that the stent and the pusher catheter may be uncoupled regardless of insertion and removal of the inner catheter, and therefore they may be inadvertently uncoupled, making it unable to pull back the stent.

Moreover, the system of Patent Document 2 is hard to be applied to a stent without a flap or a stent without a flap on the pusher catheter side.

Further, the problem of the system having a locking member or a lead-in member as in Patent Document 3 is that it increases the number of parts and complexifies the system.

Furthermore, in a system as shown in Patent Documents 1-3 wherein a filament loop is placed on or inserted through the stent from outside, through the distal end of which the inner catheter is inserted or which is locked by a locking member, the filament must be directed to the outside of the stent so that the filament is removed from the stent to place the stent where it should be. It increases the risk that the filament is caught by the stent.

SUMMARY

Accordingly, in light of the above problems associated with prior arts, an object of the present invention is to provide a stent delivery system with a simple structure, in which a stent and a catheter are not inadvertently uncoupled and can be easily uncoupled as intended.

The present invention solved the above problems by a tube stent delivery system comprising a tube stent, a pusher catheter, and an inner catheter; characterized in that a filament having a knot is tied to the distal end of said pusher catheter or said tube stent through an opening formed in a radial direction thereof, said tube stent or said pusher catheter having a catching hole in which said knot is fit loosely, said filament or said knot being inserted into said tube stent or said pusher catheter, and said inner catheter being inserted into said pusher catheter and said tube stent, with said knot being loosely fit in said catching hole; and said inner catheter supporting loose-fitting of said knot and said catching hole.

The filament preferably makes a loop through a hole of the tube stent.

Further, the filament may have a plurality of the knots.

The present invention provides a very simple structure in which a filament and a knot tied to the distal end of a pusher catheter or a tube stent through an opening formed in a radial direction thereof are inserted into the tube stent or the pusher catheter, an inner catheter being inserted into the pusher catheter and the tube stent with the knot being loosely fit in a catching hole of the tube stent or the pusher catheter, the inner catheter supporting loose-fitting of the knot and the catching hole. Such a configuration is advantageous in preventing inadvertent uncoupling of the stent and the pusher catheter, because the knot is kept to be loosely fit in the catching hole unless the inner catheter is pulled out, or the knot is blocked from going inside the pusher catheter or the stent as long as the inner catheter stays inside. Further, unlike a conventional system in which a filament needs to be directed toward the outside of the stent, the filament may be moved to the inside of the stent or the pusher catheter, because of the configuration in which the filament and the knot is inserted into the stent, the inner catheter supporting loose-fitting of the knot and the catching hole, or more specifically a state in which the knot is fitting loosely in the catching hole of the stent or the pusher catheter from inside thereof. Since the filament is inserted into the stent or the pusher catheter, when the inner catheter is pulled out and then the pusher catheter is pulled off the stent, the filament with the knot is pulled in the axial direction, which means that the knot moves by itself to the inside of the hollow stent or the pusher catheter. Accordingly, the catching hole is preferably designed to be rounded where it contacts the knot, so that the knot would not caught by the catching hole even if it touches the hole when moving.

Further, it is preferable that the filament makes a loop through the hole of the tube stent; the stent is left with the filament loop which can be caught to pull out the stent smoothly.

An embodiment with a plurality of knots is capable of preventing inadvertent uncoupling of the stent and the pusher catheter more reliably than those with only one knot.

DETAILED DESCRIPTION

With reference to FIGS. 1-6, embodiments of the present invention are to be described below. The present invention, however, is not limited to those embodiments. It should be noted that the knot is overdrawn in some of the figures for the sake of simplicity, but in fact it may have a size sufficient to make the knot loosely fit in a catching hole and to enable an inner catheter to support the loose-fitting, i.e., a size sufficient to prevent the knot from moving into the inside of a stent or a pusher catheter when the inner catheter is inserted therein.

Figure 1:
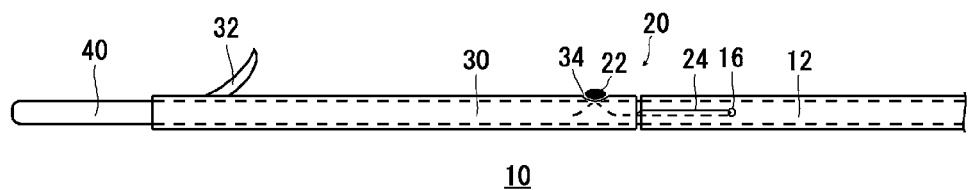
FIG. 1 is a side view of a stent kit having a first embodiment of a stent delivery system of the present invention.

A stent kit 10 in FIG. 1 comprises a pusher catheter 12, a first embodiment of a stent delivery system of the present invention (hereinafter simply referred to as a "delivery system") 20, a stent 30, and an inner catheter 40. The pusher catheter 12 has an opening 16 through which a filament 24 is tied to its distal end, and the stent 30 has a flap 32 and a catching hole 34. The catching hole 34 is larger than the knot 22 so that the knot 22 can fit loosely therein. The catching hole 34 is preferably round-shaped where it contacts with the knot 22. Although the stent kit 10 employs a straight-type stent 30, the present invention can be applied to any type of stent.

Figure 2:
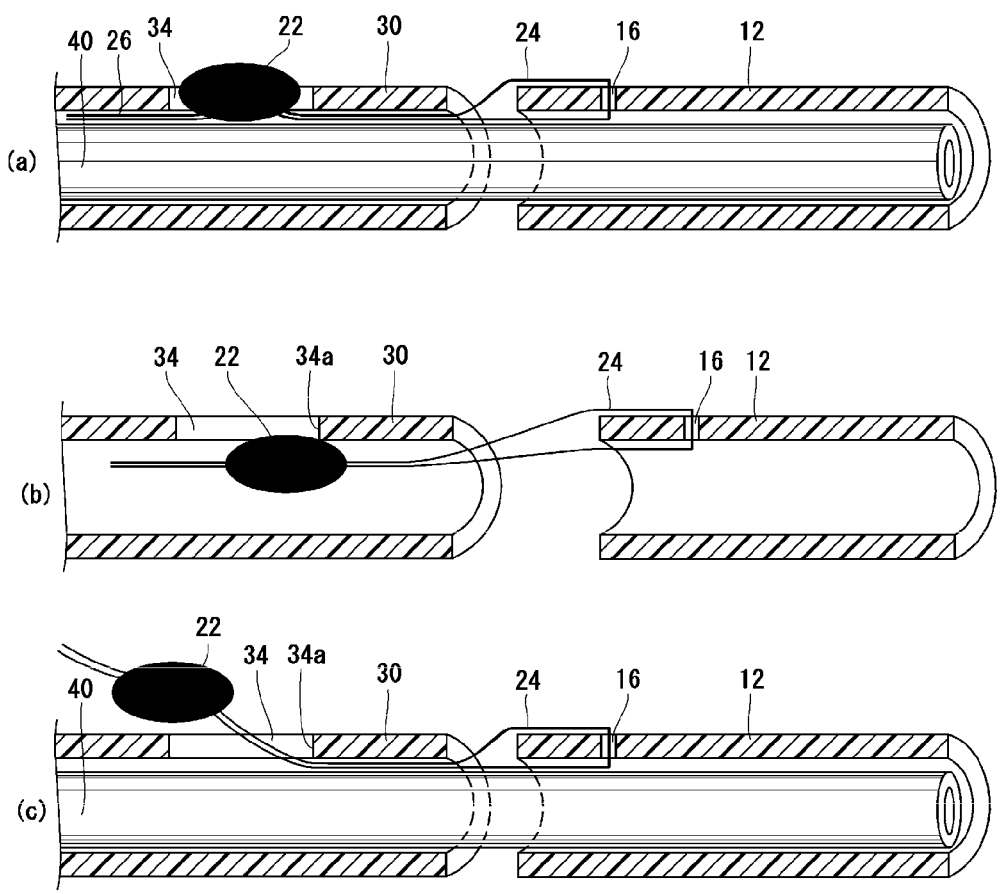
FIG. 2 is an enlarged cross-sectional view of a major part of a first embodiment of a stent delivery system of the present invention.

FIG. 2 is an enlarged cross-sectional view of a major part of a first embodiment of a stent delivery system of the present invention, wherein the stent 30 and the pusher catheter 12 are illustrated with some distance in-between for the sake of simplicity. As shown in FIG. 2 (a), the knot 22 is supported by the inner catheter 40 to be loosely fit in the catching hole 34 from inside the stent 30, so that the knot 22 cannot move into the inside of the stent 30. Accordingly, when the pusher catheter 12 is pulled back, so is the stent 30, with the knot 22 being caught by the catching hole 34. Having such a highly simple structure, the system of the present invention works with a fewer parts, and the stent 30 and the pusher catheter 12 are less likely to be uncoupled inadvertently unless the inner catheter 40 is pulled out, because the inner catheter securely supports the knot 22 loosely fitting in the catching hole 34.

FIG. 2 (b) illustrates the pusher catheter 12 being pulled out after the inner catheter 40 was pulled out. As shown in (b), as the pusher catheter 12 is pulled out, the filament 24 inserted in the stent 30 is strained, which generates component force to move the knot 22 to the inside of the stent 30. The knot 22 is less likely to be caught by the catching hole 34 by shaping the catching hole 34 so as to have a round side wall 34a where the knot 22 contacts with the catching hole 34. As shown in (a), when the distal end 26 of the filament 24 is inserted in the stent 30 so as to have the filament 24 extend beyond the hole 34 as viewed from the side of pusher catheter 12, the knot 22 is pushed outward from the hole 34 to the outside of the stent 30. This is advantageous in that the knot 22 would move back to the inside of the stent 30 by itself, when the inner catheter 40 is pulled out.

Further, in this invention, the knot 22 is prevented from being completely pushed out of the stent 30, because the distal end 26 of the filament 24 extends beyond the catching hole 34 as viewed from the side of pusher catheter 12, meaning that the filament 24 is sandwiched between the stent 30 and the inner catheter 40 on both sides of the hole 34. In other words, the present invention solves the problem that the knot 22 is completely pushed out of the stent 30 and caught by the side wall 34a of the catching hole 34 when the pusher catheter 12 is pulled out. Designed to be inserted into a twisty human body, the stent 30 and the pusher catheter 12 are given an allowance in-between, and the filament 24 is also given a corresponding allowance. When the allowance given to the filament 24 is big relative to the distance between the opening 16 into which the filament 24 is inserted and the catching hole 34, as shown in FIG. 2 (c), the knot 22 may be caught by the side wall 34a of the catching hole 34 when the pusher catheter 12 is pulled out. Therefore, it is preferable that the allowance of the filament 24 is small relative to the distance between the opening 16 into which the filament 24 is inserted and the catching hole 34.

Figure 3:
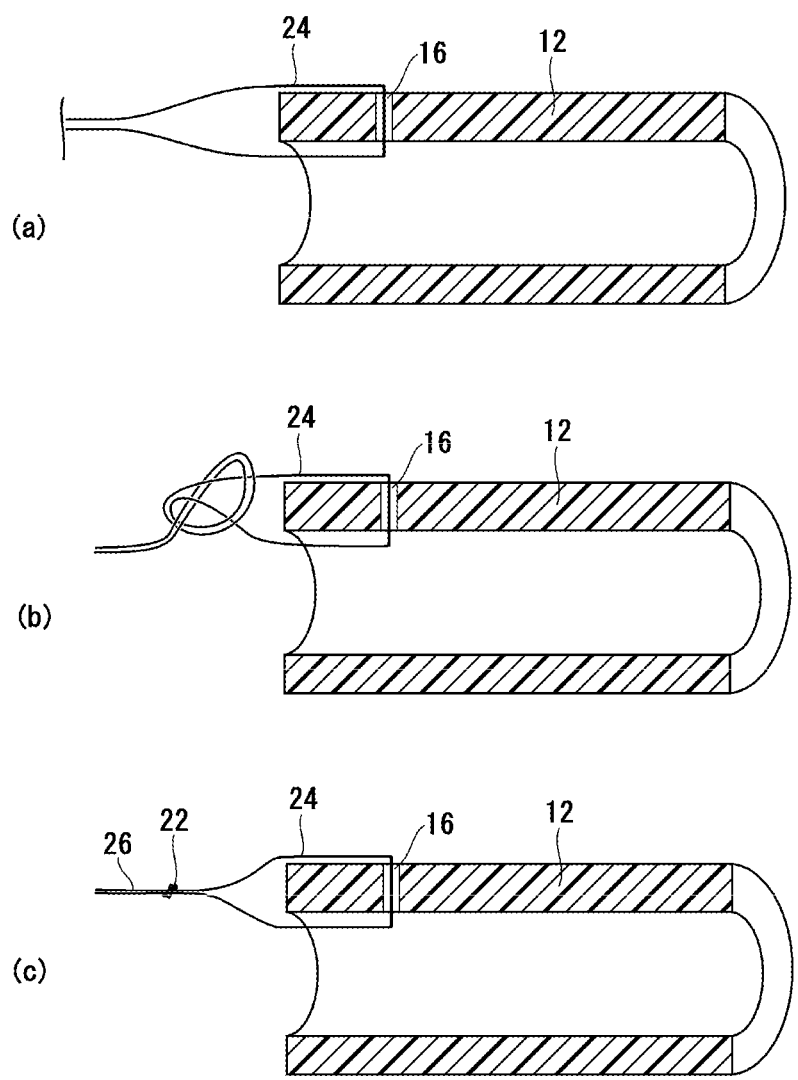
FIG. 3 illustrates an example of steps to tie a filament in a first embodiment of the present invention.

FIG. 3 illustrates an example of steps to tie the filament 24 to the pusher catheter 12 in a first embodiment of the present invention. The filament 24 is tied to the pusher catheter 12 by inserting the filament 24 through the opening 16 formed in a radial direction of the pusher catheter 12 as shown in (a), and by making a knot as shown in (b). Thus the knot 22 is created as shown in (c), which can be used as the "knot". Preferably, the knot 22 is hardened with adhesive or resin to utilize it as the "knot," so that the knot 22 will not be unknitted and will become round or oval. The filament 24 may have the distal end 26, because the knot 22 might come untied when the distal end 26 of the filament 24 is too short.

Figure 4:
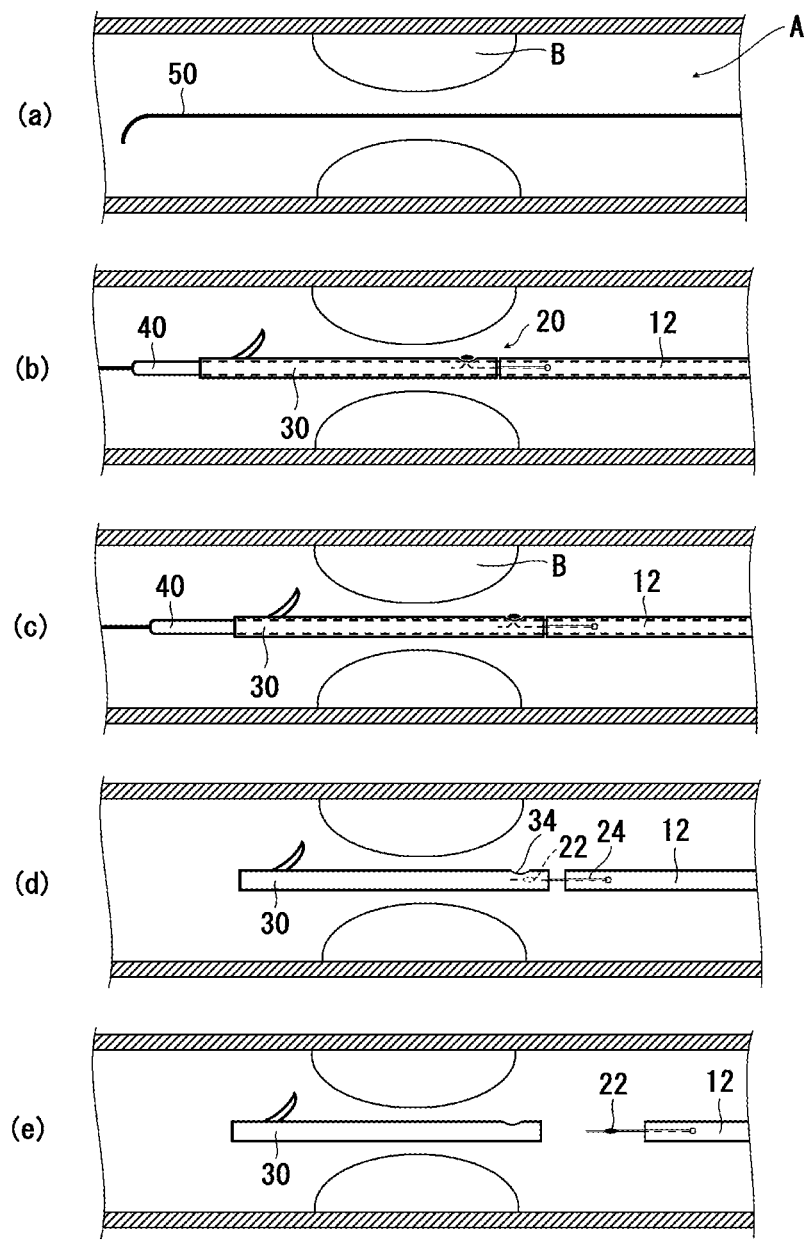
FIG. 4 illustrates steps to place a stent kit having a first embodiment of a stent delivery system of the present invention.

FIG. 4 illustrates steps to place the stent 30 where it should be. By way of example, in order to place the stent 30 in the strictured area B of a bile duct A, a guide wire 50 is first inserted into the bile duct A pass the strictured area B as shown in (a). Then as illustrated in (b), the inner catheter 40 is inserted along the wire 50, and along the inner catheter 40, the stent 30 and the pusher catheter 12 having the stent delivery system 20 of the present invention are inserted. The next step is shown in (c), in which the pusher catheter 12 is controlled to have the stent 30 go back and forth in order to decide the position to place the stent 30 in relation to the strictured area B. The wire 50, the inner catheter 40, the stent 30, and the pusher catheter 12 are all inserted into a human body through a lumen of an endoscope not shown in the figure, and the positioning of the stent 30 is carried out by means of the endoscope. Here, the stent 30 moves forward by being pushed by the pusher catheter 12, and moves back as the pusher catheter 12 is pulled back and the knot loosely fit in the catching hole of the stent 30 is caught by the catching hole. When positioning is completed, the guide wire 50 and the inner catheter 40 are pulled out. As illustrated in (d), when the pusher catheter 12 is pulled out, the knot 22 is pulled toward the inside of the stent 30 and the knot 22 is released from the hole 34. Thus, the filament need not to be directed to the outside of the stent as in conventional arts, and therefore the stent 30 and the pusher catheter 12 can be uncoupled more easily. When the pusher catheter 12 is pulled out completely in this state, the stent 30 is placed where it is as shown in (e).

Since a patient lies on his/her back or in the left lateral decubitus position in most cases, the stent kit is used in a nearly-horizontal condition.

Figure 5:
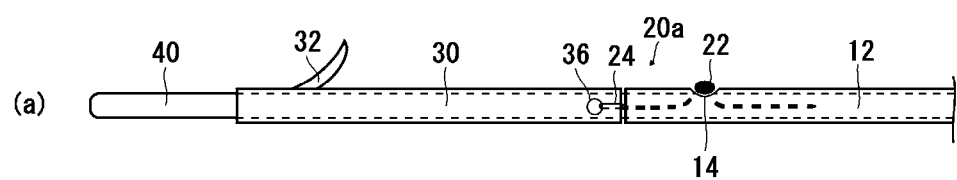
FIG. 5 is a side view of a stent kit having a second embodiment of a stent delivery system of the present invention.

FIG. 5 is a side view of a stent kit 10a having a stent delivery system 20a of a second embodiment of the present invention. As illustrated in (b), the filament 24 is pierced through the opening 36 and tied to make a loop, and the tie forms the knot 22. The filament 24 is then inserted into the pusher catheter 12 as shown in (a), wherein the filament 24 extends beyond the catching hole 14 as viewed from the side of the stent 30, and the knot 22 is loosely fit in the catching hole 14, the condition being supported by the inner catheter 40. That the filament 24 preferably has a small allowance between the opening 36 through which the filament 24 is tied and the catching hole 14, and preferable shapes of the knot 22 are the same as previously mentioned.

FIG. 5 (b) illustrates how the delivery system 20a looks when the stent 30 is placed where it should be. Namely, with the loop filament 24 being left with the stent 30, the stent 30 can be easily pulled out by catching the filament 24. The knot 22 may be formed as an extension of the loop.

Figure 6:
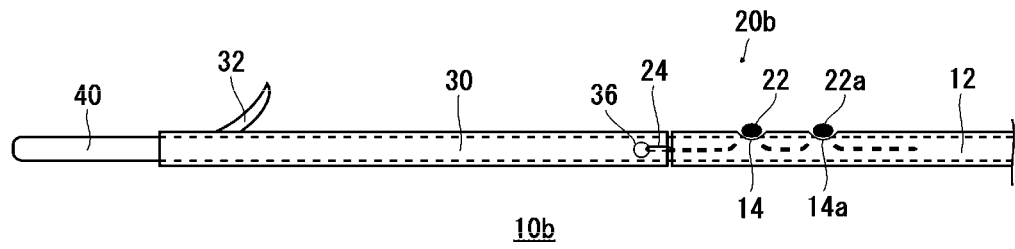
FIG. 6 is a side view of a stent kit having a third embodiment of a stent delivery system of the present invention.

Lastly, FIG. 6 is a side view of a stent kit 10b having a stent delivery system 20b of a third embodiment of the present invention. As shown in FIG. 6, because the knots 22, 22a are designed to loosely fit in the catching holes 14, 14a on the pusher catheter 12 respectively, with the filament 24 extending beyond the catching holes 14, 14a as viewed from the side of the stent 30, the loose-fitting of the knots 22, 22a and the catching holes 14, 14a can be more securely maintained, meaning that inadvertent uncoupling of the stent 30 and the pusher catheter 12 can be prevented. The filament 24 has preferably a small allowance between the opening 36 through which the filament 24 is tied and the catching holes 14, 14a.

As explained above, having a simply structure in which a filament carrying a knot is tied to a hole of a pusher catheter or a stent, the filament or the knot is inserted into the stent or the pusher catheter, and as an inner catheter is inserted into the stent and the pusher catheter with the knot loosely fit in a catching hole of the stent or the pusher catheter from inside, the present invention can provide a stent delivery system with a fewer parts, and in which a stent and pusher catheter are not inadvertently uncoupled and can be easily uncoupled as intended.

What is claimed is:

1. A tube stent delivery system comprising:
a tube stent;
a pusher catheter;
an inner catheter; and
a filament having a knot that is tied to a distal end of said pusher catheter through an opening formed in a radial direction thereof,
said tube stent having a catching hole provided through said tube stent in a radial direction and in which said knot is fit loosely,
said filament and said knot being inserted into said tube stent, the filament inserted into the tube stent being wholly inside of the tube stent, and said inner catheter being inserted into said pusher catheter and said tube stent, with said knot being loosely fit in said catching hole a distal end of said filament extends beyond said catching hole toward a distal end of said tube stent to prevent the knot from being completely pushed out of the pusher catheter through the catching hole; and
said inner catheter supporting loose-fitting of said knot in said catching hole.

2. A tube stent delivery system as claimed in claim 1 wherein said filament makes a loop through an opening of said pusher catheter.

3. A tube stent delivery system as claimed in claim 2 wherein said tube stent has a plurality of catching holes and said filament has a plurality of knots being loosely fit in each catching hole.

4. A tube stent delivery system as claimed in claim 1, wherein said tube stent has a plurality of catching holes and said filament has a plurality of knots being loosely fit in each catching hole.

5. A tube stent delivery system as claimed in claim 1 wherein said catching hole is larger than the knot so that the knot can fit loosely therein.

6. A tube stent delivery system comprising:
a tube stent;
a pusher catheter;
an inner catheter; and
a filament having a knot that is tied to a proximal end of said tube stent through an opening formed in a radial direction thereof,
said pusher catheter having a catching hole provided through said pusher catheter in a radial direction and in which said knot is fit loosely,
said filament and said knot being inserted into said pusher catheter, the filament inserted into the pusher catheter being wholly inside of the pusher catheter, and said inner catheter being inserted into said pusher catheter and said tube stent, with said knot being loosely fit in said catching hole a distal end of said filament extends beyond said catching hole toward a proximal end of said pusher catheter to prevent the knot from being completely pushed out of the pusher catheter through the catching hole; and
said inner catheter supporting loose-fitting of said knot in said catching hole.

7. A tube stent delivery system as claimed in claim 6 wherein said filament makes a loop through an opening of said tube stent.

8. A tube stent delivery system as claimed in claim 7 wherein said pusher catheter has a plurality of catching holes and said filament has a plurality of knots being loosely fit in each catching hole.

9. A tube stent delivery system as claimed in claim 6 wherein said pusher catheter has a plurality of catching holes and said filament has a plurality of knots being loosely fit in each catching hole.

10. A tube stent delivery system as claimed in claim 6 wherein said catching hole is larger than the knot so that the knot can fit loosely therein.

* * * * *